United States Patent [19]

Podolsky et al.

[11] 4,205,129
[45] May 27, 1980

[54] METHOD FOR PURIFYING GALACTOSYLTRANSFERASE ISOENZYMES AND PRODUCT

[75] Inventors: Daniel K. Podolsky, Boston, Mass.; Milton M. Weiser, Buffalo, N.Y.

[73] Assignee: The Massachusetts General Hospital, Boston, Mass.

[21] Appl. No.: 17,288

[22] Filed: Mar. 5, 1979

[51] Int. Cl.² ............................................. C07G 7/026
[52] U.S. Cl. .................................. 435/193; 435/815; 424/94
[58] Field of Search ................... 435/193, 815; 424/94

[56] References Cited

PUBLICATIONS

Podolsky et al., Biochemical and Biophysical Research Communication, vol. 65, No. 2, pp. 545–551, Jul. 1975.

*Primary Examiner*—Lionel M. Shapiro
*Attorney, Agent, or Firm*—Thompson, Birch, Gauthier & Samuels

[57] ABSTRACT

Pure galactosyltransferase isoenzyme GT-II having a molecular weight of about 71,000 is obtained from malignant cells or tumors of animals and humans. The GT-II is isolated by subjecting a body fluid or extract of the malignant cells or tumors containing the isoenzyme and GT-I galactosyltransferase isoenzyme to serial column separation steps and utilizing materials in the column which resemble cofactors for galactosyltransferase GT-II.

6 Claims, 6 Drawing Figures

METHOD FOR PURIFYING GALACTOSYLTRANSFERASE ISOENZYMES AND PRODUCT

BACKGROUND OF THE INVENTION

This invention relates to a pure galactosyltransferase isoenzyme, GT-II and to the method for its purification.

The enzymes known generically as glycosyltransferases participate in the biosynthesis of complex carbohydrates. They are commonly found as both membrane-bound enzymes within the interior of the cell and as soluble enzymes in biological fluids. The function of adding sugars to proteins is not clear, although the nature of the terminal sugar appears to be important in the control of secretion and in the clearance of circulating glycoproteins, the control of differentiation and cell-cell interaction. The biosynthesis of ABO blood group substances also requires sugar additions through the action of glycosyltransferases. Although some glycosyltransterases appear to be membrane-associated enzymes when prepared from tissue homogenates, these transferases have also been detected as soluble enzymes in various body fluids, including rat and human serum.

It has been reported in Biochemical and Biophysical Research Communications, Vol. 65, No. 2, pp. 545–551 and Proceedings of the National Academy of Sciences, U.S.A., Vol. 73, No. 4, pp. 1319–1322 that there exists two isoenzymes of serum galactosyltransferase. The isoenzyme identified as GT-II was shown to be found predominantly in patients with neoplastic disease. There is a correlation of serum GT-II levels with the extent of malignancy which apparently is independent of the site of the neoplasm. The preoperative level of GT-II activity appears to correlate with the overall extent of the tumor. Thus, the level of serum GT-II increases in association with the progression of the disease. It is not known whether the galactosyltransferase (GT-II) is merely produced by the cancerous cells or is somehow involved in the mechanism of concerous cell reproduction.

It is also shown in U.S. patent application, Ser. No. 948,252, filed Oct. 3, 1978, entitled "Method and Composition for Inhibition of Growth of Transformed Cells and Tumors", that a substrate for the galacosyltransferase isoenzyme (GT-II) also has the characteristic of inhibiting growth or destroying concerous cells and/or cancerous tumors. The inhibitor is found present in the cancerous cells or malignant tumors or in the body fluids such as sera of animals, including humans which are afflicted with cancer. The inhibitor also is found in vitro in transformed animal cells. The inhibitor is obtained by subjecting either the body fluid containing the inhibitor or the fluid obtained from malignant cells to a separation procedure which includes a step for concentrating glycoproteins from the fluid being treated and at least one chromatographic step in order to recover a fraction of glycoprotein having a molecular weight of about 3600±3000.

It would be highly desirable to provide pure GT-II galactosyltransferase isoenzyme thereby to provide a means for producing and harvesting an antibody for GT-II. Such an antibody would be useful in means for assaying for GT-II if the GT-II used to form the antibody were sufficiently pure. Furthermore, such an antibody would be useful for inhibiting growth of cancerous cells and/or cancerous tumors as does the naturally-occurring inhibitor for GT-II.

SUMMARY OF THE INVENTION

This invention provides pure galactosyltransferase isoenzyme, GT-II, which is sufficiently pure so that it can be used to produce the antibody to the GT-II. The antibody, in turn, can be utilized to provide a means to assay for the GT-II such as by radioimmunoassay. The pure GT-II is obtained by affinity chromatography of a protein fraction containing GT-II obtained from cancerous cells, tumors taken from an animal, e.g. a human, or biological fluids from tumor-bearing animals, e.g. humans. The GT-II recovered has a molecular weight of 71,000±10,000.

DESCRIPTION OF SPECIFIC EMBODIMENTS

Figure 1:
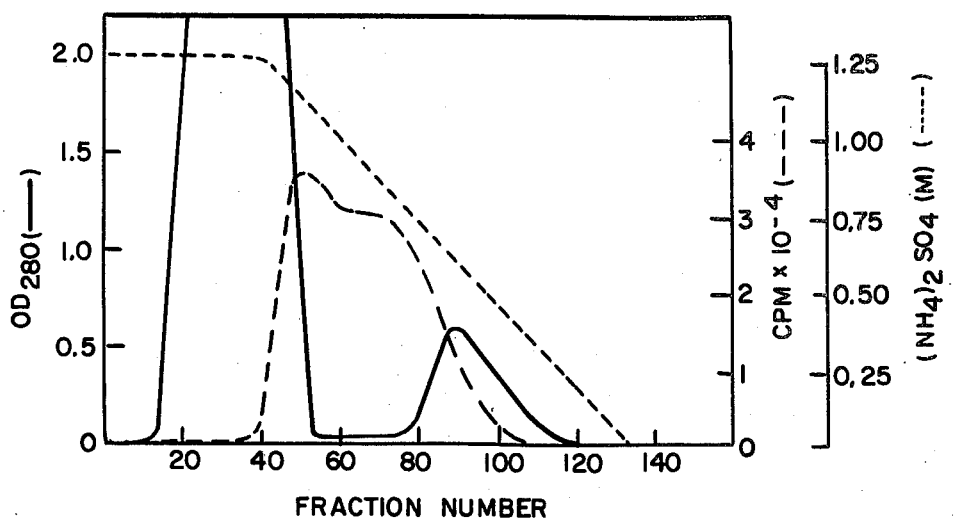

The purified galactosyltransferase isoenzyme, GT-II, of this invention is obtained from animal body fluids containing the GT-II such as serum or from malignant cells or malignant tumors either in vivo or in vitro. In a preliminary step, the body fluid can be admixed with a composition which precipitates a protein fraction containing the GT-II which is isolated by centrifugation. The liquid containing the inhibitor is subjected to at least two serial separations in a column. In one column, the separating material comprises a composition which functions to isolate galactosyltransferases from the remaining components in the fluid being separated. The second column contains a separating material which functions chromatographically to separate the different galactosyltransferases (e.g. GT-I and GT-II) in the body fluid being treated, generally on the basis of molecular weight, thereby to isolate a galactosyltransferase fraction having a molecular weight of about 71,000±10,000. In the process of this invention, the sequence of galactosyltransferase isolation and separation of the different galactosyltransferases is not critical; that is, the galactosyltransferase isolation can precede the chromatographic separation of the different galactosyltransferases or vice versa. While the product of this invention can be purified substantially 100% by multiple chromatographic steps, it has been found that only 2 chromatographic steps are sufficient in order to obtain the separated enriched GT-II product. Thus, the product of this invention can contain components of the body fluid or cell extract which do not adversely affect the ability of the GT-II to promote formation of its specific antibody in subsequently employed procedures.

Representative suitable materials which function to separate galactosyltransferases from other constituents in body fluids include a polymeric material having bound thereto a cofactor or a composition that functions as a cofactor for galactosyltransferases. Materials which function as such cofactors include $\beta$-lactalbumin, ovalbumin, N-acetylgalactosamine, fetuin, glucose, UDP-galactose or UMP. These cofactor-like materials can be bound to polymeric material such as Sephadex, Sepharose, Agarose, polyacrylamide or the like. Representative suitable materials which function to separate body fluids, generally on the basis of molecular weight in order to obtain a fraction having a molecular weight of about 71,000± about 10,000, include DEAE cellulose, Sephadex, Sepharose, polyacrylamide, membrane ultrafilters or the like.

In a preferred embodiment of the process of this invention, galactosyltransferase isolating steps precede and follow the chromatographic galactosyltransferase step in order to rapidly achieve a large degree of purification. In addition, improved purity of GT-II is obtained by utilizing additional galactosyltransferase isolation steps. In any event, the GT-II is obtained sufficiently pure so that it exhibits a specific activity of at least $1 \times 10^5$ pmoles/mg protein/60 min, preferably at least about $1 \times 10^7$ pmoles/mg protein/60 min as measured in the manner described below.

In the procedure of this invention, a suspension of the body fluid containing GT-II is formed by separating the solid portion of the cells and/or tumors and treating the resulting fluid to form a fraction rich in GT-II. Generally, this is effected by utilizing a composition that causes proteins to precipitate such as ammonium sulfate, lead or organic solvent extraction. The concentration of precipitant is varied and the precipitate obtained from each fraction is tested for galactosyltransferase activity such as in the manner described below and the active fractions are pooled and resuspended such as in a solution of ammonium sulfate, sodium cacodylate, organic solvent or other buffer and passed through the columns described above. The bound GT-II is eluted from the column with a conventional salt gradient such as sodium phosphate, sodium cacodylate or ammonium sulfate. The fractions recovered are monitored for GT-II activity.

The purified GT-II of this invention can be used to produce antibodies to GT-II which, in turn, can be utilized to assay body fluids for the presence of GT-II. Since GT-II has been found to be associated selectively with animals having malignant cells or tumors, such an assay is useful for the detection of cancer in animals. The antibody can be utilized in any conventional assay techniques such as radioimmunoassay wherein the antibody can be labeled with a radioactive isotope. Alternatively, the antibody can be utilized in conventional electrophoresis techniques wherein a positive test for GT-II is determined by an agglutination reaction.

The antibody to the pure GT-II of this invention is produced by injecting the pure GT-II into the blood system of an animal such as a rabbit for an incubation period sufficient to permit the animal's system to produce the antibody to the GT-II. Generally suitable dosages for injection are between about 25 micrograms and 5000 micrograms, usually about 100 micrograms and 1000 micrograms per animal. Generally, the GT-II dosage is administered by multiple injections of subunits of the dosage in order to permit the animal to elicit a high concentration of serum antibodies to the GT-II. Suitable incubation periods for forming the antibody are conventional and generally are between about 1 week and 2 months, usually between about 2 and 4 weeks. The animal then is bled and the serum containing the antibody then is separated by any conventional means such as by centrifugation. The serum then is chromatographed through a column reservoir such as diethylaminoethyl cellulose to isolate the antibody.

Suitable animals for forming the antibody are goat, horse, rabbit, chicken or other animals normally used for producing sera.

The following example illustrates the present invention and is not intended to limit the same.

EXAMPLE I

This example illustrates the preparation of galactosyltransferase isoenzyme, GT-II, and of galactosyltransferase isoenzyme, GT-I.

Assay of Galactosyltransferase Activities - UDP-[$^3$H]galactose (2.25 Ci/mmole) was purchased from New England Nuclear. A stock solution, 714 $\mu$M, was prepared to a final specific activity of 0.228 Ci/mmole using unlabeled UDP-galactose obtained from Sigma Chemical Co.

The assay mixture included 10 $\mu$l of sample, 7.5 $\mu$l of UDP-[$^3$H]galactose stock solution, 25 $\mu$l of 0.1 M sodium cacodylate pH 7.4 and 0.154 M NaCl, 7.5 $\mu$l of 0.1 M MnCl$_2$ and 20 $\mu$l of the acceptor SGF-fetuin which contained 0.2 $\mu$m acceptor sites. The mixture (75 $\mu$l) was incubated for 60 min. at 37°. The reaction was terminated by addition of 5% phosphotungstic acid (w/v) in 2 M HCl, and incorporation of radioactive label into acid precipitable material was determined as described by Podolsky et al, Biochem. Biophys. Res. Comm., 65, 545–551, (1975). Galactosyltransferase enzyme activity may als be determined using N-acetylglucosamine and glucose as substrate acceptors in the presence or absence of $\alpha$-lactalbumin (1-mM) in place of SGF-fetuin utilizing paper electrophoresis. After incubation, reaction mixtures are applied to Whatman 1 MM and paper electrophoresis performed in 1% tetraborate buffer to isolate the reaction product as described by Weiser, J. Biol. Chem., 248, 2536–2541, (1973).

Detection of Isoenzymes GT-I and GT-II - Polyacrylamide gel electrophoresis of samples for detection of galactosyltransferase isoenzyme activity were performed by the method of Podolsky and Weiser, 1974, (above) with two modifications. First, effusion samples (1.0 ml) were dialyzed against 0.01 M sodium cacodylate, pH 7.4, with 0.015 M NaCl and subsequently concentrated ten-fold by drying under nitrogen prior to the application of 25 $\mu$l of the concentrated sample. Second, the specific activity of the donor UDP-[$^3$H]galactose used in the galactosyltransferase assay was increased to 0.228 Ci/mmole as above and the assay mixture was adjusted to incorporate a 25 $\mu$l sample in a total reaction volume of 150 $\mu$l. Isoenzyme GT-I was defined as that activity migrating with Rf$_{alb}$=0.30–0.50, while GT-II was defined as that activity migrating with Rf$_{alb}$=0.08 as established by Podolsky and Weiser, 1974, (above).

Preparation of Acceptor - Fetuin from which terminal sialic acid and penultimate galactose residues were removed (SGF-fetuin) was prepared as described by Kim et al, J. Biol. Chem., 246, 5466–5476 (1971). Ovalbumin, a uniform N-acetylglucosaminyl acceptor, was obtained from Sigma Chemical Co. and used without further modification. Ovine submaxillary mucin, a uniform N-acetylgalactosaminyl acceptor after removal of terminal sialic acid (Sf-OSM), N-acetylglucosamine and glucose also were utilized as acceptors.

Chromatography and Polyacrylamide Gel Electrophoresis - Descending paper chromatograph was done on Whatman 3MM paper with the following solvent systems: A, pyridine—ethyl acetate-water—acetic acid (5:5:3:1 by vol.; 24 h); B, butanol—pyridine water (10:5:4 by vol 16 h). Reducing sugars were detected on the chromatograms by the alkaline-AgNO$_3$ reaction as described by Trevelyan et al, Nature, 166, 444–445, (1950).

Analytical polyacrylamide gel electrophoresis was carried out by using the electrophoretic system described for separation of isoenzymes GT-I and GT-II. SDS-polyacrylamide gel chromatography for molecular weight determinations was carried out by the method of Fairbanks et al, Biochemistry, 10, 2607–2617, (1971). Molecular weight standards included horse heart cytochrome C (M.W. 11,700), DEP-trypsin (M.W. 23,300), egg albumin (M.W. 43,000), 7S rabbit gamma globulin (M.W. HC=50,000, LC=23,500), bovine serum albumin (M.W. 68,000), phosphorylase (M.W. 98,000) and E. Coli β-galactosidase (M.W. 120,000). Protein was stained by Coomassie Blue and carbonhydrate detected by using the periodic acid Schiff reagent as described by Steck et al, Science, 168, 255–257. Molecular weight determinations by chromatography on Biogel P-150 obtained from BioRad Co., Inc. were performed on a column (1.5 cm × 60 cm) developed with 0.1 M Na cacodylate pH 7.4 at a flow rate of 20 ml/hr collecting 5 ml fractions which were assayed for protein and galactosyltransferase as described.

Purification of Isoenzymes GT-I and GT-II - Malignant effusions (pleural, ascitic and pericardial) were obtained after cytologic examination. Only cytology-positive malignant effusions were found to contain both GT-I and GT-II enzyme activities. These effusions were pooled for a final volume of 8–9 liters and cells and debris removed by centrifugation at 1000 × g for 30 min. Mercaptoethanol (to 1 mm) and 0.1% w/v sodium azide were added to the pooled material. Subsequently, ammonium sulfate was added over a 20 min period with stirring at 4° to 30% saturation (182.5 g/l). The solution was stirred for 3 hr and the precipitated protein was removed by centrifugation for 45 min at 14,000 × g. The supernatant was made to 70% saturation by addition of ammonium sulfate (240 g/l) over 20 min in the cold with stirring. The solution was allowed to stand at 4° overnight and the precipitate was subsequently collected by centrifugation for 45 min at 14,000 g. The supernatant was discarded and the precipitate suspended in approximately 300 ml of 0.02 M Tris-HCl, pH 7.5, 0.001 M mercaptoethanol and 1.25 M ammonium sulfate.

Norleucine-Sepharose 4B Chromatography - Norleucine-Sepharose 4B was prepared by modification of the method of Geren et al, Arch. Biochem. Biophys., 172, 149–155, (1976). 30 g of CNBr-Sepharose 4B, obtained from Pharmacia Co., was washed first in 6 l of 0.001 M HCl and then 0.5 M NaHCO$_3$, pH 8.0, with 0.5 M NaCl. The moist gel then was added to 800 mg norleucine in 140 ml of the coupling buffer comprising 0.5 M NaHCO$_3$ pH 8.0 with 0.5 M NaCl. After incubation at room temperature for 180 min, the gel was washed and then incubated in 150 ml of 1 M ethanolamine, pH 8.0, for 120 min at room temperature. The norleucine-Sepharose 4B was then washed with three cycles of alternating 0.1 M acetate buffer, pH 4.0, in 1 M NaCl and 0.05 M NaHCO$_3$, pH 8.0, in 1 M NaCl. Finally, the gel was washed extensively in 0.02 M Tris-HCL, pH 7.5, with 0.001 M mercaptoethanol, 1.25 M ammonium sulfate. The norleucine-Sepharose 4B gel was estimated to contain approximately 15 μmole amino acid/ml gel by determination of amino acid concentration before and after coupling using the ninhydrin method described by Moore et al, J. Biol. Chem., 176, 367–375, (1948).

Chromatography with norleucine-Sepharose 4B was accomplished with a decreasing ammonium sulfate gradient. The 30–70% ammonium sulfate cut obtained from the pooled effusions was applied to a 1.5×60 cm column. The column was washed with 150 ml of the application buffer followed by a linear decreasing ammonium sulfate gradient (1.25–0.00 M) in 0.02 M Tris HCL, pH 7.5, and 0.001 M mercaptoethanol, at a flow rate of 32 ml/hr, collecting 5 ml fractions. All fractions were subsequently dialyzed extensively against 0.01 M sodium cacodylate, pH 7.4 and 0.15 M NaCl prior to evaluation of galactosyltransferase activity and an estimation of protein by measuring optical density at 280 mμ using a Gilford spectrophotometer. This separation step is not critical and, if desired, can be eliminated or replaced with a column utilizing a cofactor-like material for GT-II such as N-acetylglucosamine or β-lactalbumin bound to Sepharose.

DEAE-Cellulose Chromatography - Fractions from the norleucine-Sepharose 4B column which demonstrated galactosyltransferase activity were pooled for a total volume of 600 ml to which 170 g ammonium sulfate were added in the cold. The precipitate was collected and then resuspended in 2.5 ml of 0.0005 M sodium phosphate buffer, pH 7.6. The sample was dialyzed extensively against this buffer prior to application to a column (2.5×100 cm) of DEAE-cellulose equilibrated in the application buffer. An additional 300 ml of buffer was run through the column at a rate of 35 ml/hr, collecting 10 ml fractions. Chromatography was continued with a linear gradient of 0.0005 M to 0.1 M sodium phosphate buffer, pH 7.6, over 48 hr. The elution was followed by continuous UV monitoring, (OD$_{280}$), and analysis of each fraction for galactosyltransferase activity after dialysis against 0.1 M sodium cacodylate, pH 7.4. Two separate peaks demonstrating galactosyltransferase activity were separately pooled and subsequently assayed for isoenzyme composition by the polyacrylamide electrophoretic method described above. The peaks, continuing GT-I and GT-II activities exclusively, were each subjected to further purification.

α-Lactalbumin Sepharose 4B Chromatography - Activities in peaks I (75 ml) and II (275 ml) were concentrated by precipitation with 30 g and 110 g of ammonium sulfate, respectively. The separate precipitates were then dissolved in 5.0 ml of 0.06 M N-ethyl-morpholine (NEM) buffer, pH 8.0, containing 0.05 M N-acetylglucosamine, 0.02 M NaCl and 0.025 mM UDP-galactose and then dialyzed exhaustively against this buffer. Alpha-lactalbumin-Sepharose 4B was prepared as described by Andrews, FEBS Letters, 9, 297–300, (1970) using a bovine α-lactalbumin. Affinity chromatography was carried out by modification of the method of Geren et al, Arch. Biochem. Biophys., 172, 149–155. Individual columns (0.9×30 cm, void vol: 6 ml) were prepared for chromatography of the individual samples I and II and washed with the described buffer. The samples were then applied to the columns and, after the samples had entered their respective columns, the flow was stopped by clamping the columns for 30 min. Subsequently, the columns were washed with 100 ml of the application buffer, collecting 7.5 ml fractions. The columns were then eluted with 0.06 M NEM buffer, pH 8.0, containing 0.004 M EDTA. Again, the columns were clamped for 30 min after the new elution buffer had entered the column prior to continuous elution. Fractions were evaluated for protein by the method of Lowry et al., J. Biol. Chem., 193, 265–275, (1951) and for galactosyltransferase activity after dialysis against 0.1 M sodium cacodylate, pH 7.4. Galactosyltransferase activity was eluted almost exclusively in a single peak from each column and the fractions comprising these peaks were pooled.

N-acetylglucosamine-Sepharose 4B Chromatography - Activity in peaks I (15 ml) and II (21 ml) were dialyzed against 0.1 M sodium cacodylate, pH 7.3, containing 0.025 M NaCl, 0.002 M UMP and 0.001 M mercaptoethanol. The samples were then applied at room temperature to individual columns (0.9×30 cm) which contained p-aminophenylglucosamine covalently attached to Sepharose 4B by the method of Bloch et al, FEBS Letters, 44, 286–289, (1956). The columns were equilibrated with the application buffer and each sample was applied in 5.0 ml fractions, clamping the columns for 30 min between successive application. Subsequently, the columns were washed with 100 ml of application buffer with continuous elution at 30 ml/hr. The application buffer was then changed to an elution buffer containing 0.1 M sodium cacodylate, pH 7.3, 0.024 M EDTA, 0.005 M N-acetylglucosamine, 0.001 M mercaptoethanol and 0.5 M urea. After two void volumes had entered the column (total volume 15 ml), flow was again stopped for 30 min followed by continuous elution at 30 ml/hr as before, collecting 5.0 ml fractions. Protein and galactosyltransferase were assayed as before, and the fractions containing enzyme activities were pooled.

Figure 2:
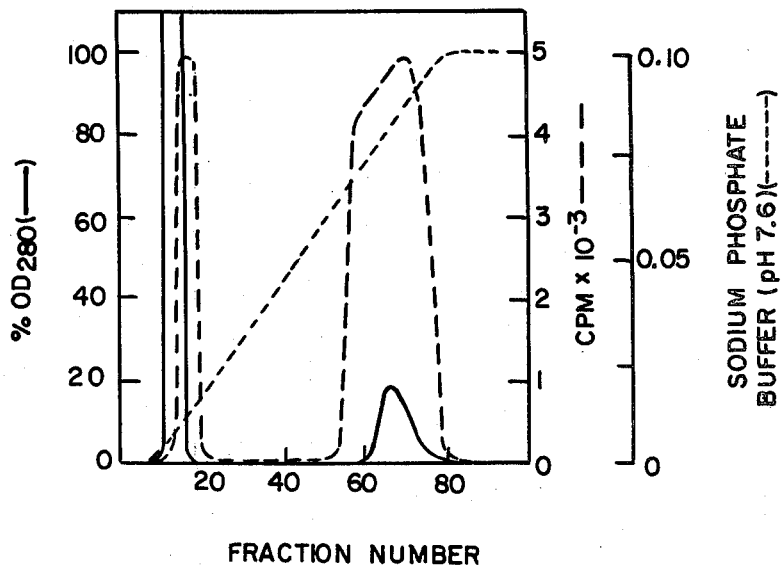

As a result of the purification, two electrophoretically distinct forms of galactosyltransferase activity found in cytology-positive malignant effusions analogous to the isoenzymes GT-I and GT-II found in serum from the majority of patients with malignant diseases were obtained in a purified form. In order to obtain a source of sufficient quantity for purification of these two activities, cytology-positive effusions were obtained and evaluated for the presence of the cancer associated GT-II as well as the normal isoenzyme GT-I. Those effusions containing both isoenzymes were then pooled and an initial 2.5-fold purification was obtained by ammonium sulfate precipitation. This material was then applied to a column of norleucine-Sepharose 4B and using a descending $(NH_2)_4SO_4$ gradient, galactosyltransferase activity was eluted as one major peak (FIG. 1). This step achieved a further purification to 15-fold but failed to separate the two galactosyltransferase activities as revealed by polyacrylamide electrophoresis. Subsequently, the two activities were separated and further purified by chromatography on DEAE-cellulose, eluting with an ascending phosphate concentration. As FIG. 2 shows, the pooled galactosyltransferase activity eluted from norleucine-Sepharose 4B could be separated into two peaks of activity. The earlier eluting galactosyltransferase activity (fractions 11–20) from this column was shown to co-electrophorese with Gt-I activity without any detectable GT-II. Galactosyltransferase activity eluted at high ionic strength (fractions 55–80) co-migrated on polyacrylamide electrophoresis exclusively with GT-II activity found in whole serum or in effusions of patients with cancer.

Figure 3:
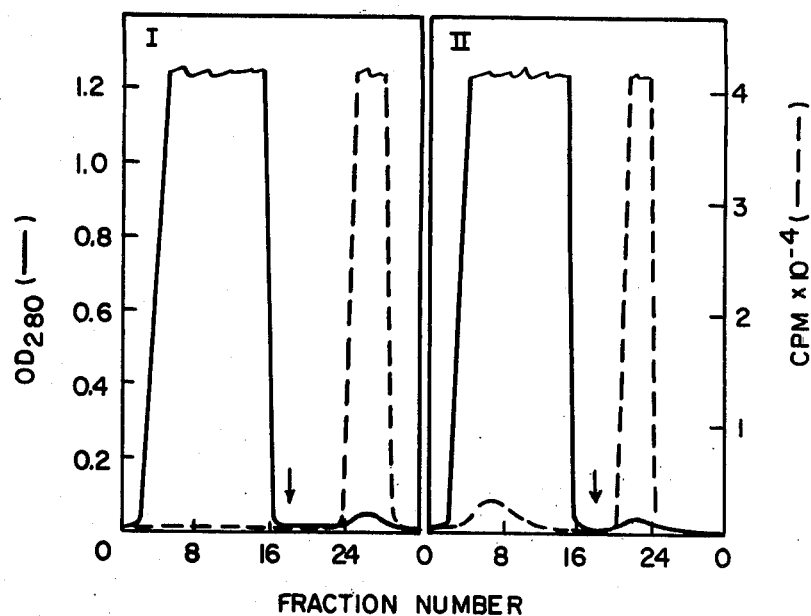

The different activities (I and II) were individually subjected to further purification steps by a sequence of two affinity columns. The first of these entailed chromatography on Sepharose 4B to which α-lactalbumin, a protein modifier of galactosyltransferase activity, had been covalently linked. The results of this step are shown in FIG. 3 which shows that each activity from the DEAE column (both I and II) could be selectively removed from α-lactalbumin columns. These activities were again shown to co-migrate with GT-I and GT-II respectively.

Figure 4:
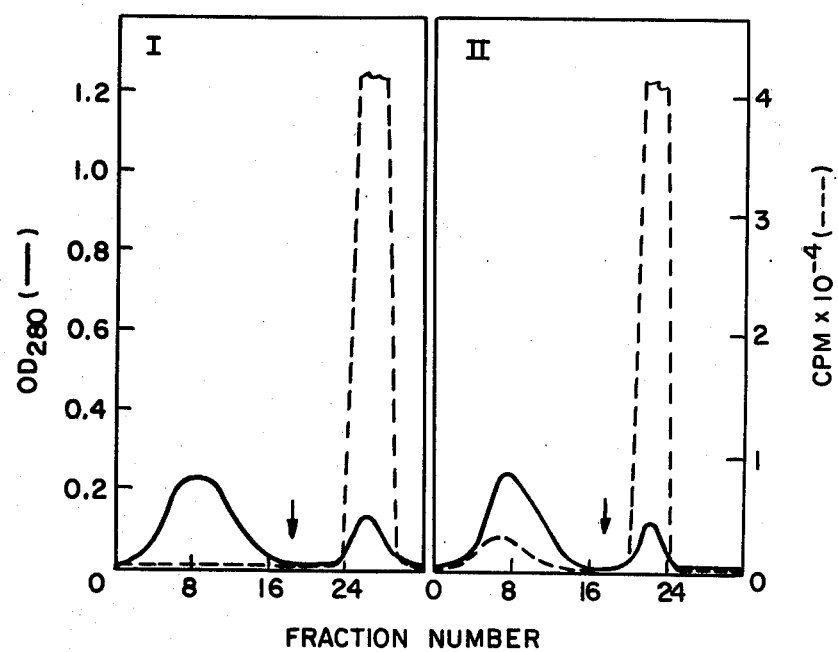

Finally, the two activities were separately chromatographed on columns of Sepharose 4B to which N-acetylglucosamine, a substrate analogue for galactosyltransferase activities had been bound through a phenyl derivative. FIG. 4 shows that both galactosyltransferase activities were again specifically eluted in a buffer containing a competitive substrate and EDTA, and again the peaks eluted from each N-acetylglucosamine-Sepharose 4B column were found to coelectrophorese with GT-I and GT-II respectively. Protein straining of polyacrylamide gels with Coomassie Blue confirmed that the separated purified galactosyltransferase activities contained but a single protein band which co-migrated with the enzymatic activity. In view of their homogeneity by both enzyme assay and protein staining and their migratory characteristics, the galactosyltransferase activities eluted from the N-acetylblucosamine-Sepharose 4B columns were considered to represent purified GT-I and GT-II. Table I details the overall results of the purification of GT-I and GT-II and indicates that they were enriched 4300 and 5400-fold, respectively.

Kinetic and Compositional Characterization - The purified activities, GT-I and GT-II, were subsequently subjected to kinetic and compositional characterization. Electrophoresis of the two activities on SDS-polyacrylamide gels again confirmed the homogeneity of the separated enzyme activities. Incorporation of radioactively labeled galactose into product by both isoenzymes was shown to be linearly related to time of incubation (up to 240 min), the amount of enzyme added, and the amount of substrate. In addition, SDS-polyacrylamide gel electrophoresis allowed approximation of molecular weight of 54,000 and 76,000 for GT-I and GT-II respectively using the method of Fairbanks et al., Biochemistry, 10, 2605–2617. Molecular weight determinations were confirmed by chromatography with Biogel P-150 obtained from BioRad Co. which again showed elution of the individual isoenzymes as single symmetrical peaks of activity and yielded values of M.W. calc GT-I=56,000 and M.W. calc GT-II=71,000.

Both GT-I and GT-II were found to have an absolute dependence on the presence of divalent cation for enzymatic activity. By far the most efficient cation was $Mn^{++}$ but modest activity could be detected in the presence of either $Co^{++}$ or $Cd^{++}$ for both enzymes (Table II). Optimum concentrations of $MnCl_2$ was found to be 10 μM for both GT-I and GT-II. Both enzyme activities were found to be active over a broad pH range (6.0–8.0). Maximum activity was detected in the range of pH 7.0–7.3.

Figure 5:
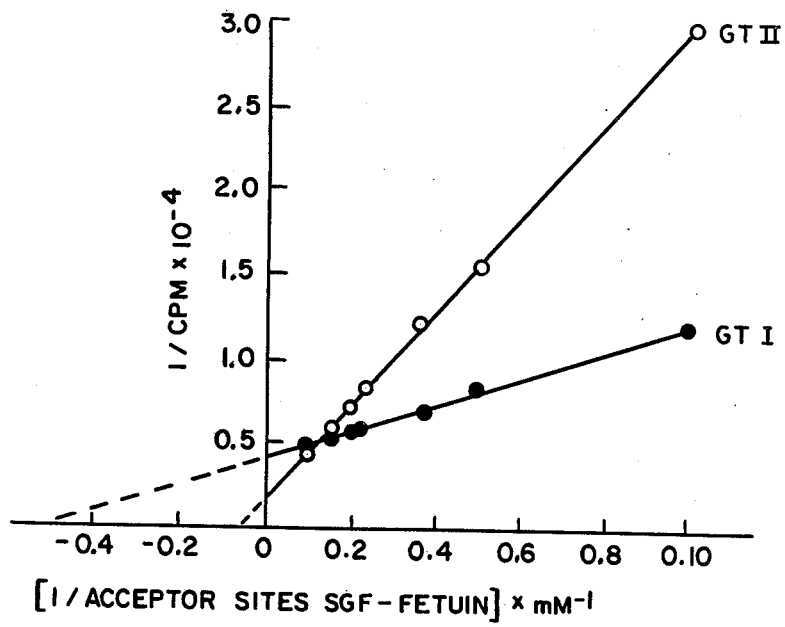

The affinities (Km) of GT-I and GT-II were determined for nucleotide-sugar donor (UDP-galactose) and for acceptors (ovalbumin, SGF-fetuin, N-acetylglucosamine, glucose, SF-OSM) using Lineweaver-Burk plots. Km UDP-galactose was found to be $1.3 \times 10^{-5}$ M for both GT-I and GT-II. Similarly, GT-I and GT-II had identical affinity for the acceptor substrate ovalbumin ($2 \times 10^{-3}$ M). Both enzymes were inactive toward SF-OSM, an acceptro with terminal N-acetylgalactosaminyl residues. However, as demonstrated in FIG. 5, there was an order of magnitude difference in the Km SGF-fetuin between GT-I ($2 \times 10^{-4}$ M) and GT-II ($2 \times 10^{-3}$ M). In addition, both enzymes were evaluated for substrate specificity in the presence and absence of α-lactalbumin. As Table III demonstrates, in the absence of the modifier protein, both enzymes preferentially utilized glucosamie over glucose as substrate. Addition of α-lactalbumin to the reaction mixture reduced isoenzyme I utilization of the hexosamine in favor of glucose. In contrast, the relative decrease in glucosamie substrate activity of isoenzyme II was much less marked as demonstrated in Table III.

Figure 6:
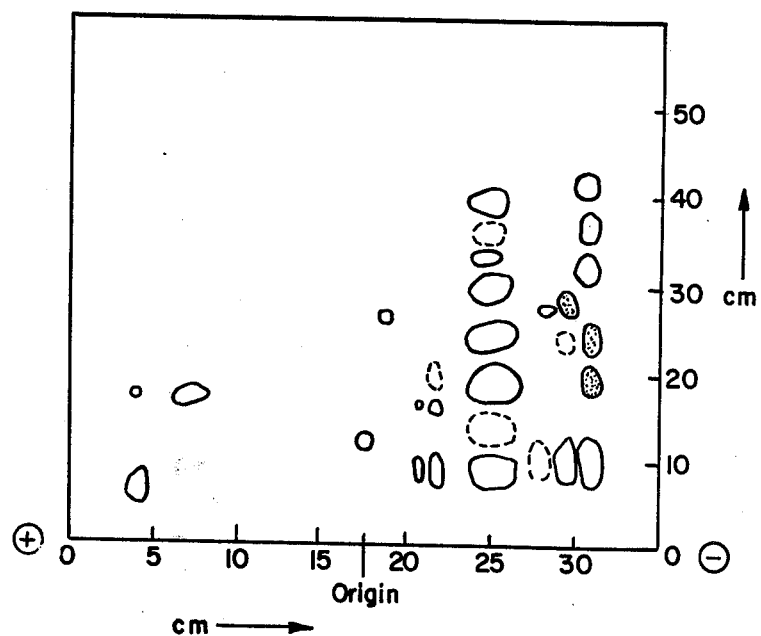

In addition to kinetic parameters, both purified GT-I and GT-II were analyzed for amino acid and carbohydrate composition. Relative concentration of component amino acids were determined using gas-liquid chromatographic techniques. Results of the amino acid analysis are given in Table IV, with data expressed as residues per 1,000 amino acids. As Table IV indicates, although minor differences are found in the concentration of several of the amino acids, there is no single major difference to distinguish GT-I from GT-II on the basis of amino acid composition; large amounts of glycine were observed in both enzymes. However, tryptic peptide map analysis revealed distinct differences in composition of GT-I and GT-II as demonstrated in FIG. 6. While the two enzymes contained several peptides of identical mobility, each also possessed peptides not found in the other.

Both GT-I and GT-II were found to contain detectable carbohydrate by chemical assay and g.l.c. analysis. As Table V documents, GT-II was found to possess twice (9%) the carbohydrate content as GT-I (4%) and nearly all of this difference could be accounted for by an increase in hexosamine content in GT-II relative to GT-I. No significant amounts of sialic acid could be detected in either GT-I or GT-II. Complementary data were obtained by g.l.c. carbohydrate analysis which documented the presence of mannose, glucosamine and small amounts of galactose in both enzymes. Again, the difference in carbohydrate composition was found to be largely accounted for by differences in glucosamine content. In addition, qualitative evaluation of sugar content by descending chromatography, performed after acid hydrolysis of the purified isoenzymes, confirmed the presence of amnnose, glucosamine and galactose and did not detect additional sugars.

Of particular note are the findings on SDS-polyacrylamide gel electrophoresis which clearly demonstrate a difference in molecular weight between GT-I and GT-II. Although glycoproteins with high carbohydrate content have been known to exhibit anomalous behavior during SDS-polyacrylamide electrophoresis, the relatively low percentage of carbohydrate in GT-I and GT-II, together with the high gel concentration used in these studies (12.5%) make it unlikely that the large difference in molecular weight observed between GT-I and GT-II is due to an artifact of electrophoresis. The validity of these determinations is supported by results from Biogel P-150 chromatography. The normal, smaller GT-I has a molecular weight similar to other purified galactosyltransferases including that for human whey and rat mesenteric lymph node while GT-II is larger than that reported for most purified soluble galactosyltransferase enzymes. In addition, this example shows that each isoenzyme is made of single polypeptide without component subunits as indicated by their homogeniety in SDS-polyacrylamide gel electrophoresis.

Analysis of amino acid and carbohydrate composition reveal a similar content for both GT-I and GT-II, with high concentrations of glycine in both. As noted above, peptide map analysis shows several similarities as well as differences between the two activities. Of note is the carbohydrate composition which is limited to glucosamine, mannose and galactose. In contrast to other purified galactosyltransferases, notably bovine milk galactosyltransferase, only small amounts of galactosamine could be found and there was no detectable sialic acid. The cancer-associated GT-II was found to have significantly more glucosamine than GT-I.

Finally, the kinetic characteristics of the two activities GT-I and GT-II may be contrasted. In most respects, the requirements for enzyme activity and substrate affinity were similar for the two galactosyltransferases, as well as to those reported for other purified galactosyltransferases. While both enzyme activities required manganese cation for maximum activity, in contrast to other galactosyltransferase activities, this requirement was not absolute and partial activity could also be observed in the presence of cobalt or cadium.

The only substantial kinetic differences between GT-I and GT-II lay in their differential affinity for the acceptor SGF-fetuin and their relative sensitivity to the modifier protein α-lactalbumin. This is of particular interest in view of the observation that the two enzymes had identical Km for N-acetylglucosamine alone, which is also the proximate acceptor sugar in SGF-fetuin. The difference in Km SGF-fetuin indicates the ability for the more extended glycoprotein structure to influence its efficiency as an acceptor for sugar in SGF-fetuin.

TABLE I

Purification of Galactosyltransferase Isoenzymes from Malignant Effusion

| Fraction | Volume | Protein | Sp. Act. | Yield | Purification |
|---|---|---|---|---|---|
| | ml | mg/ml | pmole/mgl 60 min | % | |
| Pooled effusion | 8540 | 42.0 | $1.1 \times 10^4$ | 100 | 1 |
| Ammonium sulfate 30–70% | 480 | 19.0 | $2.8 \times 10^4$ | 84 | 2.5 |
| Norleucine-Sepharose | 600 | 2.4 | $1.6 \times 10^5$ | 91 | 15 |
| DEAE-Cellulose | | | | | |
| Peak "I" | 75 | 9.6 | $7.2 \times 10^6$ | 58 | 65 |
| Peak "II" | 275 | 0.7 | $1.3 \times 10^7$ | | 120 |
| α-Lactalbumin-Sepharose 4B | | | | | |
| Peak "I" | 15 | 0.18 | $2.3 \times 10^8$ | 41 | 2100 |
| Peak "II" | 22 | 0.08 | $3.2 \times 10^8$ | | 2900 |
| GlcNac-Sepharose 4B | | | | | |
| Peak "I" | 35 | 0.03 | $4.2 \times 10^8$ | 28 | 4300 |
| Peak "II" | 40 | 0.02 | $5.4 \times 10^8$ | | 5400 |

TABLE II

Effect of Cation Substitutes on Galactosyltransferase Activity

| Cation | GT-I cpm/10 μl/60 min | GT-II cpm/10 μl/60 min |
|---|---|---|
| EDTA | 120 | 140 |
| $Mn^{++}$ | 8410 | 8020 |
| $Mg^{++}$ | 90 | 140 |
| $Zn^{++}$ | 130 | 130 |
| $Ca^{++}$ | 160 | 120 |
| $Cd^{++}$ | 2250 | 1970 |
| $Co^{++}$ | 2090 | 1690 |
| $K^+$ | 160 | 140 |

| Enzymes | α-lactalbumin | Substrate* Glucose | Glucosamine |
|---|---|---|---|
| GT-I | − | 0.6 | 7.2 |
| | + | 4.2 | 0.9 |
| GT-II | − | 1.1 | 6.8 |
| | + | 2.7 | 3.2 |

*Activity expressed as μmole of galactose transferred per mg of protein.

| Amino Acid | Residues/100 amino acids | |
|---|---|---|
| | GT-I | GT-II |
| Alanine | 86.4 | 65.1 |
| Valine | 63.9 | 54.4 |
| Gyline | 330.9 | 369.5 |
| Isoleucine | 13.0 | 20.5 |
| Leucine | 65.9 | 55.6 |
| Proline | 18.8 | 19.4 |
| Threonine | 31.5 | 34.8 |
| Serine | 48.0 | 63.7 |
| Phenylalanine | 47.9 | 56.9 |
| Asparagine/aspartic acid | 49.2 | 82.9 |
| Glutamine/glutamic acid | 94.1 | 108.5 |
| Lysine | 105.4 | 73.3 |
| Cysteine | 11.1 | 15.0 |
| Tyrosine | 13.2 | 13.0 |
| Tryptophan | 12.0 | 13.7 |
| Histidine | 8.9 | 15.5 |
| Arginine | — | — |
| Hydroxylysine | — | — |

| Method | Carbohydrate | Mole/Mole Enzyme | |
|---|---|---|---|
| | | GT-1 | GT-II |
| Assay | Neutral Hexose | 8.5 | 11.2 |
| | Hexosamine | 6.9 | 17.2 |
| | Sialic Acid | <0.1 | 0.1 |
| Glc | Fucose | 0.5 | 0.8 |
| | Galactose | 2.2 | 3.1 |
| | N-Acetyl-D-Glucosamine | 7.2 | 16.4 |
| | N-Acetyl-D-Galactosamine | 0.1 | 0.2 |
| | Mannose | 7.6 | 9.2 |

We claim:

1. A composition of matter derived from the body fluids of animals having cancer or from extracts of malignant cells or tumor which comprises:
 a galactosyltransferase isoenzyme having a molecular weight of about 71,000 and having an activity of at least about $1 \times 10^5$ pmole/mg protein/60 min.

2. The composition of claim 1 which is derived from the extract of malignant cells or tumors.

3. The composition of claim 1 which is derived from a body fluid of an animal having cancer.

4. The process for isolating a galactosyltransferase isoenzyme having a molecular weight of about 71,000 which comprises isolating a body fluid or an extract of malignant cells or a malignant tumor containing a galactosyltransferase isoenzyme having a molecular weight of about 71,000, passing said body fluid or extract serially through two separation columns, one of said columns containing a material comprising a cofactor for said isoenzyme or a material that resembles a cofactor for said isoenzyme to concentrate said isoenzyme in said body fluid or extract and the other of said columns containing a material which concentrates components in said body fluid or extract having a molecular weight of about 71,000.

5. The process of claim 4 wherein said body fluid or extract is passed first through the column containing the material concentrates components in said body fluid or extract having a molecular weight of about 71,000.

6. The process of claim 4 wherein said body fluid or extract is passed through at least one additional column containing a cofactor for said isoenzyme or a material that resembles a cofactor for said isoenzyme.

* * * * *